(12) United States Patent
Alfieri

(10) Patent No.: US 9,451,980 B2
(45) Date of Patent: Sep. 27, 2016

(54) HAND ACCESS DEVICE

(71) Applicant: Covidien LP, Mansfield, MA (US)

(72) Inventor: Francesco Alfieri, Lincoln, RI (US)

(73) Assignee: Covidien LP, Mansfield, MA (US)

( * ) Notice: Subject to any disclaimer, the term of this patent is extended or adjusted under 35 U.S.C. 154(b) by 131 days.

(21) Appl. No.: 13/950,320

(22) Filed: Jul. 25, 2013

(65) Prior Publication Data

US 2013/0310651 A1  Nov. 21, 2013

Related U.S. Application Data

(63) Continuation of application No. 13/223,659, filed on Sep. 1, 2011, now abandoned.

(60) Provisional application No. 61/424,761, filed on Dec. 20, 2010.

(51) Int. Cl.
*A61B 17/34* (2006.01)
*A61B 17/00* (2006.01)

(52) U.S. Cl.
CPC .. *A61B 17/3423* (2013.01); *A61B 2017/00265* (2013.01); *A61B 2017/3429* (2013.01)

(58) Field of Classification Search
CPC ............... A61B 17/3423; A61B 2017/3429; A61B 2017/00265
USPC ............ 600/202–215; 604/167.04, 167.06; 606/108, 191, 213
See application file for complete search history.

(56) References Cited

U.S. PATENT DOCUMENTS

| | | | |
|---|---|---|---|
| 3,402,710 A | 9/1968 | Paleschuck |
| 4,016,884 A | 4/1977 | Kwan-Gett |
| 4,183,357 A | 1/1980 | Bentley et al. |
| 4,402,683 A | 9/1983 | Kopman |
| 4,863,438 A | 9/1989 | Gauderer et al. |
| 5,159,921 A | 11/1992 | Hoover |
| 5,242,415 A | 9/1993 | Kantrowitz et al. |
| 5,366,478 A | 11/1994 | Brinkerhoff et al. |
| 5,375,588 A | 12/1994 | Yoon |
| 5,391,156 A | 2/1995 | Hildwein et al. |
| 5,437,683 A | 8/1995 | Neumann et al. |
| 5,460,170 A | 10/1995 | Hammerslag |
| 5,480,410 A | 1/1996 | Cuschieri et al. |
| 5,490,843 A | 2/1996 | Hildwein et al. |
| 5,514,133 A | 5/1996 | Golub et al. |

(Continued)

FOREIGN PATENT DOCUMENTS

| | | |
|---|---|---|
| EP | 0538060 A1 | 4/1993 |
| EP | 0950376 A1 | 10/1999 |

(Continued)

OTHER PUBLICATIONS

European Search Report for corresponding European Appln. No. EP11194238 mailed Mar. 19, 2012. (4 pgs.).

*Primary Examiner* — Pedro Philogene

(57) ABSTRACT

A device for accessing a body cavity through an opening in tissue is provided. The access device includes a unitary compressible body configured to be received in an opening in tissue. The compressible body includes a central portion, an upper rim located on a proximal end of the body and a lower rim located on a distal end of the body. The central portion defines a slit configured to permit the passage of a hand therethrough in a sealing manner.

6 Claims, 3 Drawing Sheets

(56) References Cited

U.S. PATENT DOCUMENTS

| | | |
|---|---|---|
| 5,522,791 A | 6/1996 | Leyva |
| 5,524,644 A | 6/1996 | Crook |
| 5,545,179 A | 8/1996 | Williamson, IV |
| 5,556,385 A | 9/1996 | Andersen |
| 5,634,937 A | 6/1997 | Mollenauer et al. |
| 5,649,550 A | 7/1997 | Crook |
| 5,653,705 A | 8/1997 | de la Torre et al. |
| 5,672,168 A | 9/1997 | de la Torre et al. |
| 5,728,103 A | 3/1998 | Picha et al. |
| 5,741,298 A | 4/1998 | MacLeod |
| 5,803,921 A | 9/1998 | Bonadio |
| 5,813,409 A | 9/1998 | Leahy et al. |
| 5,830,191 A | 11/1998 | Hildwein et al. |
| 5,906,577 A | 5/1999 | Beane et al. |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 6,017,355 A | 1/2000 | Hessel et al. |
| 6,018,094 A | 1/2000 | Fox |
| 6,024,736 A | 2/2000 | de la Torre et al. |
| 6,033,426 A | 3/2000 | Kaji |
| 6,033,428 A | 3/2000 | Sardella |
| 6,077,288 A | 6/2000 | Shimomura et al. |
| 6,110,154 A | 8/2000 | Shimomura et al. |
| 6,142,936 A | 11/2000 | Beane et al. |
| 6,241,768 B1 | 6/2001 | Agarwal et al. |
| 6,254,534 B1 | 7/2001 | Butler et al. |
| 6,315,770 B1 | 11/2001 | de la Torre et al. |
| 6,319,246 B1 | 11/2001 | de la Torre et al. |
| 6,382,211 B1 | 5/2002 | Crook |
| 6,440,063 B1 | 8/2002 | Beane et al. |
| 6,450,983 B1 | 9/2002 | Rambo |
| 6,454,783 B1 | 9/2002 | Piskun |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,814,078 B2 | 11/2004 | Crook |
| 6,840,951 B2 | 1/2005 | de la Torre et al. |
| 6,846,287 B2 | 1/2005 | Bonadio et al. |
| 6,916,310 B2 | 7/2005 | Sommerich |
| 6,916,331 B2 | 7/2005 | Mollenauer et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 7,008,377 B2 | 3/2006 | Beane et al. |
| 7,033,319 B2 | 4/2006 | Pulford et al. |
| 7,052,454 B2 | 5/2006 | Taylor |
| 7,101,353 B2 | 9/2006 | Lui et al. |
| 7,153,261 B2 | 12/2006 | Wenchell |
| 7,163,510 B2 | 1/2007 | Kahle et al. |
| 7,195,590 B2 | 3/2007 | Butler et al. |
| 7,214,185 B1 | 5/2007 | Rosney et al. |
| 7,238,154 B2 | 7/2007 | Ewers et al. |
| 7,300,399 B2 | 11/2007 | Bonadio et al. |
| 7,331,940 B2 | 2/2008 | Sommerich |
| 7,344,547 B2 | 3/2008 | Piskun |
| 7,377,898 B2 | 5/2008 | Ewers et al. |
| 7,393,322 B2 | 7/2008 | Wenchell |
| 7,445,597 B2 | 11/2008 | Butler et al. |
| 7,473,221 B2 * | 1/2009 | Ewers et al. .................. 600/208 |
| 7,481,765 B2 * | 1/2009 | Ewers et al. .................. 600/208 |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,766,824 B2 | 8/2010 | Jensen et al. |
| 7,815,567 B2 | 10/2010 | Albrecht et al. |
| 7,837,612 B2 | 11/2010 | Gill et al. |
| 7,867,164 B2 | 1/2011 | Butler et al. |
| 7,909,760 B2 | 3/2011 | Albrecht et al. |
| 7,951,076 B2 | 5/2011 | Hart et al. |
| 7,998,068 B2 | 8/2011 | Bonadio et al. |
| 2001/0037053 A1 | 11/2001 | Bonadio et al. |
| 2003/0014076 A1 | 1/2003 | Mollenauer et al. |
| 2004/0015185 A1 | 1/2004 | Ewers |
| 2004/0092795 A1 | 5/2004 | Bonadio et al. |
| 2004/0111061 A1 | 6/2004 | Curran |
| 2004/0127772 A1 * | 7/2004 | Ewers ...................... A61B 1/06 600/212 |
| 2004/0267096 A1 | 12/2004 | Caldwell et al. |
| 2005/0020884 A1 | 1/2005 | Hart et al. |
| 2005/0096695 A1 | 5/2005 | Olich |
| 2005/0148823 A1 | 7/2005 | Vaugh et al. |
| 2005/0192483 A1 | 9/2005 | Bonadio et al. |
| 2006/0071432 A1 | 4/2006 | Staudner |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247678 A1 | 11/2006 | Weisenburgh et al. |
| 2006/0270911 A1 | 11/2006 | Voegele et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0270654 A1 | 11/2007 | Pignato et al. |
| 2007/0270882 A1 | 11/2007 | Hjelle et al. |
| 2008/0027476 A1 | 1/2008 | Piskun |
| 2008/0097162 A1 | 4/2008 | Bonadio et al. |
| 2008/0200767 A1 | 8/2008 | Ewers et al. |
| 2009/0012477 A1 | 1/2009 | Norton |
| 2009/0036745 A1 | 2/2009 | Bonadio et al. |
| 2009/0093752 A1 * | 4/2009 | Richard ............ A61B 17/3423 604/24 |
| 2009/0093850 A1 | 4/2009 | Richard |
| 2009/0137879 A1 | 5/2009 | Ewers et al. |
| 2009/0187079 A1 * | 7/2009 | Albrecht et al. ............... 600/206 |
| 2009/0204067 A1 | 8/2009 | Abu-Halawa |
| 2009/0221968 A1 | 9/2009 | Morrison et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0286484 A1 | 11/2010 | Stellon et al. |
| 2010/0298646 A1 | 11/2010 | Stellon et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0313250 A1 * | 12/2011 | Kleyman ...................... 600/123 |
| 2012/0095297 A1 * | 4/2012 | Dang ................. A61B 17/0218 600/208 |

FOREIGN PATENT DOCUMENTS

| | | |
|---|---|---|
| EP | 1312318 A1 | 5/2003 |
| EP | 2044889 A1 | 4/2009 |
| EP | 2095781 A2 | 9/2009 |
| EP | 2098182 A2 | 9/2009 |
| EP | 2181657 A2 | 5/2010 |
| EP | 2229900 A1 | 9/2010 |
| EP | 2238924 A1 | 10/2010 |
| EP | 2238925 A1 | 10/2010 |
| EP | 2248478 A1 | 11/2010 |

(56) References Cited

FOREIGN PATENT DOCUMENTS

| | | |
|---|---|---|
| EP | 2253283 A1 | 11/2010 |
| EP | 2272450 A2 | 1/2011 |
| EP | 2277464 A1 | 1/2011 |
| EP | 2292165 A2 | 3/2011 |
| WO | WO 96/36283 | 11/1996 |
| WO | WO 01/08581 A2 | 2/2001 |
| WO | WO 01/32116 A1 | 5/2001 |
| WO | WO 01/32120 A1 | 5/2001 |
| WO | WO 03/034908 A2 | 5/2003 |
| WO | WO 2004/043275 A1 | 5/2004 |
| WO | WO 2004/054456 A1 | 7/2004 |
| WO | WO 2004/075741 A2 | 9/2004 |
| WO | WO 2006/110733 A2 | 10/2006 |
| WO | WO 2008/103151 A2 | 8/2008 |
| WO | WO 2009/036343 A1 | 3/2009 |

\* cited by examiner

HAND ACCESS DEVICE

CROSS-REFERENCE TO RELATED APPLICATIONS

This application is a continuation of U.S. application Ser. No. 13/223,659 filed Sep. 1, 2011, which claims benefit of Provisional application No. 61/424,761 filed Dec. 20, 2010, and the disclosures of each of the above-identified applications are hereby incorporated by reference in their entirety.

BACKGROUND

1. Technical Field

The present disclosure relates to access devices for use in surgical procedures. More particularly, the present disclosure relates to compressible access devices configured for sealed receipt of a hand therethrough.

2. Background of Related Art

Access assemblies configured for reception through an opening or incision into a body cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing located on the proximal end of the cannula to access the body cavity in a sealing manner.

Compressible devices or assemblies configured for accessing a body cavity and permitting reception of instruments therethrough in a sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, i.e., forceps. Compression of the assembly reduces the profile of the assembly, thereby facilitating reception of the assembly into the incision. Upon release of the compressive force, the previously compressed assembly returns to an uncompressed configuration. One or more endoscopic or laparoscopic devices may then be inserted through one or more lumens in the assembly to complete a procedure.

Although advances have been made with regards to endoscopic and laparoscopic instrumentation, there is still no comparison to the dexterity and feel of one's hand. Being able to access a surgical site with a hand enables a surgeon to perform procedures that he/she would not otherwise be able to perform during a closed procedure. Thus, any procedure performed with hand access more closely resembles an open procedure, which a surgeon may be more comfortable performing.

Therefore, it would be beneficial to have a compressible access device which provides hand access for a surgeon.

SUMMARY

The present invention, in accordance with an embodiment thereof, relates to an access device comprising a unitary, compressible body configured to be received in an opening in tissue, the compressible body including a central portion, an upper rim located on a proximal end of the body and a lower rim located on a distal end of the body, wherein the central portion defines a slit configured to permit the passage of a hand therethrough in a sealing manner. The compressible body may define a substantially hour-glass shape. The upper and lower rims and the central portion may be substantially circular or substantially oval. The upper and lower rims may be substantially similar. The opening in the tissue may be an incision or a natural orifice. Each of the upper and lower rims may include a width of four inches (4") and a depth of four inches (4"). Alternatively, each of the upper and lower rims may include a width of four inches (5") and a depth of four inches (3"). The slit may include a length of at least two and one-half inches (2.5"). The compressible body may be composed of silicone, thermoplastic elastomers (TPE), rubber, foam and/or gel.

DESCRIPTION OF THE DRAWINGS

Embodiments of a compressible access device are disclosed herein with reference to the drawings, wherein.

DETAILED DESCRIPTION

Embodiments of the presently disclosed access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user. Although the access devices of the present disclosure will be described as relates to accessing an abdominal cavity through an incision in the abdominal wall, the access devices of the present disclosure may be modified for use in other closed procedures, i.e., laparoscopic, arthroscopic, endoscopic. Furthermore, the access devices of the present disclosure may be modified for use in accessing internal cavities through natural orifices, e.g., anus, vagina.

Figure 1:
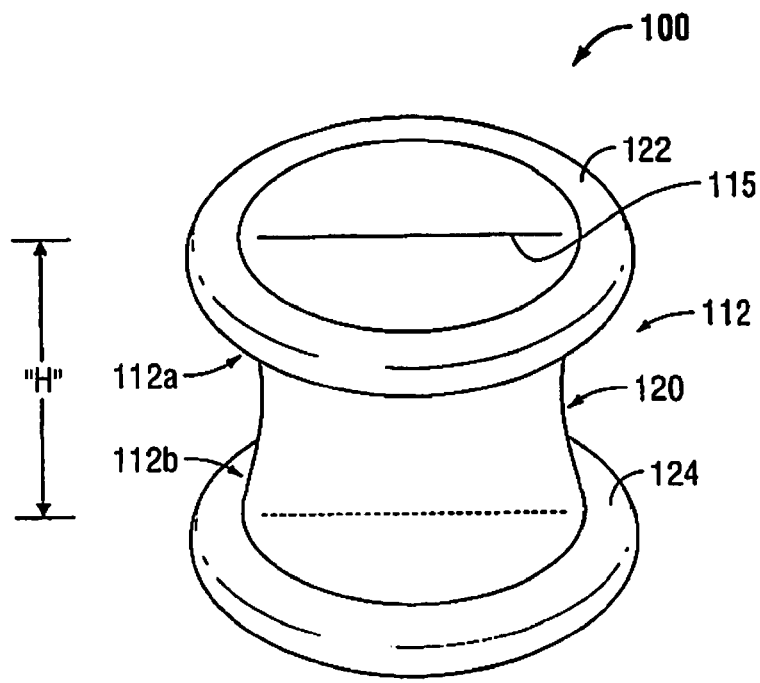
FIG. 1 is a perspective view of an embodiment of an access device according to the present disclosure.

Referring initially to FIG. 1, an access device according to an embodiment of the present disclosure is shown generally as access device 100. Access device 100 is configured for insertion through an opening in tissue, i.e., an incision, such that after insertion, access device 100 creates a seal within the opening through which a surgeon may insert and manipulate his/her hand "H" (FIG. 4) and/or one or more surgical instruments (not shown) to complete a procedure.

Figure 2:
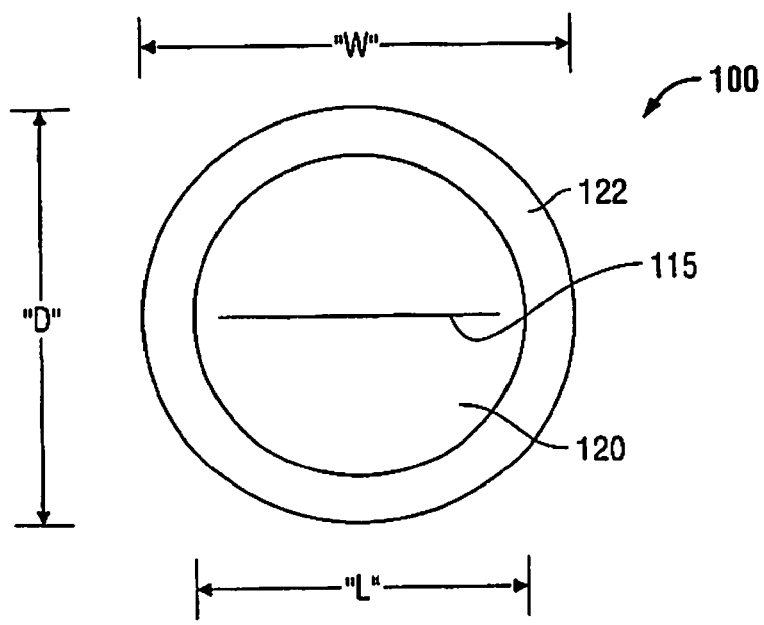
FIG. 2 is a top view of the access device of FIG. 1.

With reference to FIGS. 1 and 2, access device 100 includes a substantially compressible and/or flexible body 112. Body 112 may be formed of various materials, such as, for example, silicone, thermoplastic elastomers (TPE), rubber, foam, gel, etc. In one embodiment, body 112 includes a TPE material that is infused with an inert gas, e.g. $CO_2$ or Nitrogen, to form a foam structure. Body 112 may be coated with a lubricant, e.g. Parylene N or C, in order to create a lubricious outer surface. Various other coatings, e.g., hydrophilic, hydrophobic, bio-agents, anti-infection, analgesic, may also be employed to improve the characteristics of access device 100 or to adapt access device 100 for a specific procedure.

With reference still to FIGS. 1 and 2, body 112 includes a substantially cylindrical central portion 120, an upper rim 122 located on a proximal end 112a, and a lower rim 124 located at a distal end 112b. In this manner, body 112 defines a substantially hourglass shape when viewed from the side. Upper and lower rims 122, 124 are integrally formed with central portion 120 and define substantially annular members. Central portion 120 is configured to span the thickness of tissue "T". Upper and lower rims 122, 124 aid in preventing movement of access device 100 longitudinally through incision "I" once access device 100 has been properly received therethrough. As the thickness of tissue depends on the body composition of the patient and the location through which the underlying cavity is being accessed, the length and size of access device 100, generally, and central portion 120, specifically, may be modified to suit a given procedure. In this manner, an adult patient having fatty abdominal tissue requires an access device having a longer central portion 112 then an access assembly sized for an child.

Still referring to FIGS. 1 and 2, body 112 defines a slit 115 extending longitudinally therethrough. Slit 115 extends the length of body 112 and provides a resealable opening through which a hand "H" of a surgeon may be passed. As shown, slit 115 spans substantially the width of central portion 120. Body 112 is configured such that hand "H" may be passed through slit 115 of access device 100 while maintaining an insufflation gas within a body cavity "C". In this manner, body 112 of access device 100 forms a seal about the hand and lower arm of the surgeon, to permit sealed passage of hand "H" therethrough. Body 112 may include a coating about slit 115 to prevent tearing and/or to facilitate reception of hand "H" therethrough.

With reference still to FIGS. 1 and 2, body 112 of access assembly 100 defines a substantially hourglass shape having a height "H". Upper and lower rims 122, 124 each define substantially circular members having a width "W" and a depth "D". As shown, each of upper and lower rims 122, 124 have similar sizes and shapes, however, it is envisioned that rims 122, 124 may differ in size and/or shape. Slit 115 defines a planar opening spanning a length "L" of central portion 120. The size of access device 100 is needed to be large enough to permit passage of hand "H" through slit 115 without tearing of body 112, however, access device 100 should not be so large as to create an unnecessarily large opening in tissue "T" of the patient that may be difficult to close and/or may leave a decidedly large scar. As the size of a hand "H" differs from surgeon to surgeon, access device 100 may be provided in various sizes to accommodate the surgeon. In one embodiment, width "W" and depth "D" of first and second rims 122, 124 and height "H" of body 112 each measure between three inches (3") and five inches (5"), and preferably, four inches (4"). In the same embodiment, slit 115 includes a length "L" of at least two and one-half inches (2.5").

The use of access device 100 will now be described with reference to FIGS. 3 and 4. The following discussion will include the use of access device 100 for accessing a body cavity "C" through an incision "I" in tissue "T". As discussed above, access device 100 may be used for accessing various cavities or lumen through other openings, including naturally occurring orifices, e.g., anus.

Figure 3:
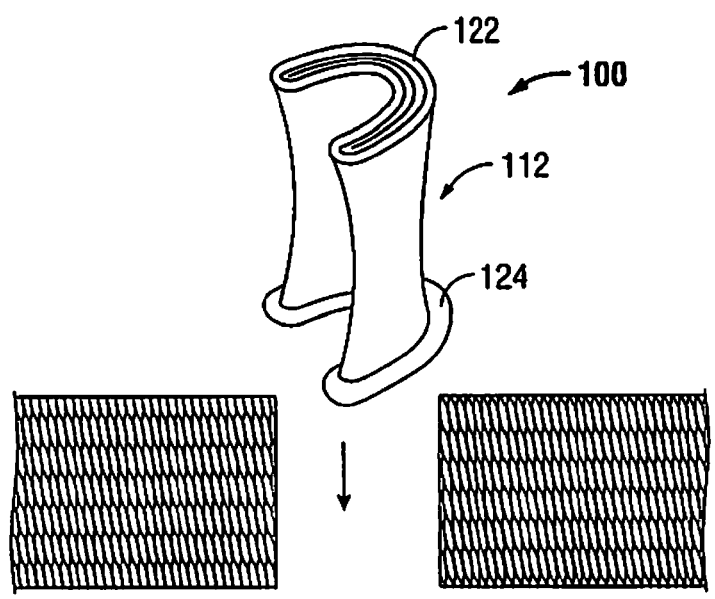
FIG. 3 is a perspective view of the access device of FIGS. 1 and 2, in a compressed condition prior to insertion through an incision.

Referring initially to FIG. 3, an incision "I" is created in tissue "T" through which access device 100 is to be inserted to access body cavity "C". Body 112 of access device is then compressed to reduce the profile of access device 100. This may be accomplished by hand or instead, through the use of an insertion mechanism (not shown). By reducing the profile of access device 100, access device 100 may be more easily inserted through incision "I".

Figure 4:
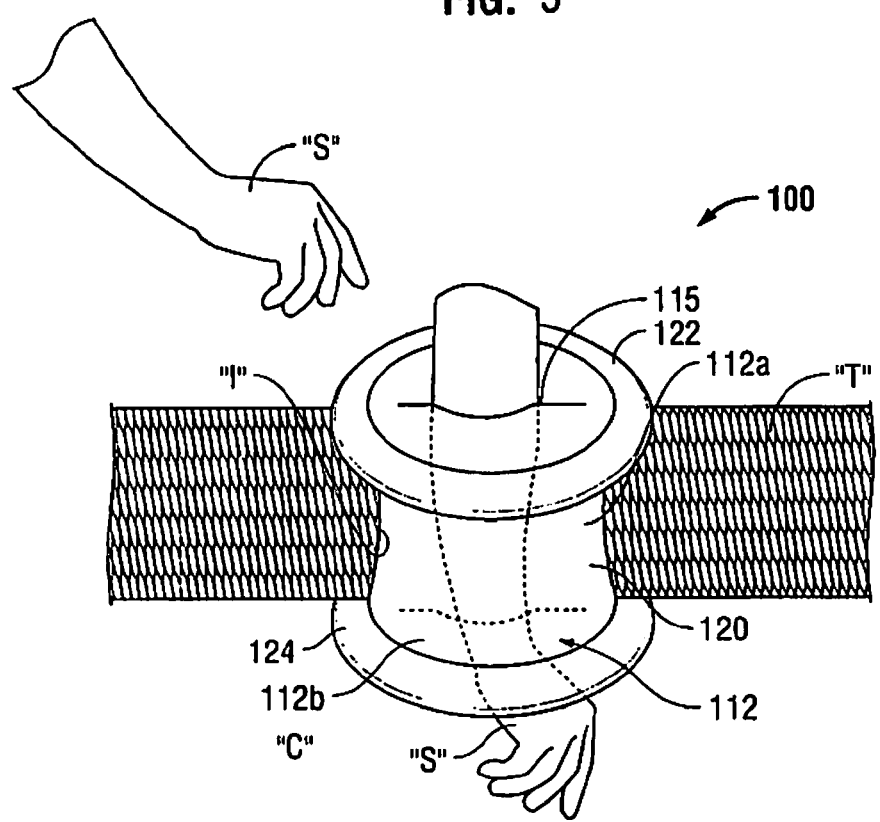
FIG. 4 is a perspective view of the access device of FIGS. 1-3, selectively secured within an incision.

Turning to FIG. 4, once received through incision "I", body 112 of access device 100 is permitted to return to an initial, uncompressed condition. Decompression of access device 100 causes access device 100 to expand within incision "I", thereby effectively sealing body cavity "C". Once sealed, body cavity "C" may be insufflated and access device 100 operates in a manner similar to traditional access assemblies configured for use with surgical instruments.

Removal of access assembly 100 from within incision "I" occurs in the reverse order of insertion. Body 112 is once again compressed to reduce the profile of access device 100. Once compressed, access device 100 may be readily withdrawn from incision "I". Once access assembly 100 is removed from incision "I", incision "I" is closed in a conventional manner, i.e., sutures, staples.

Figure 5:
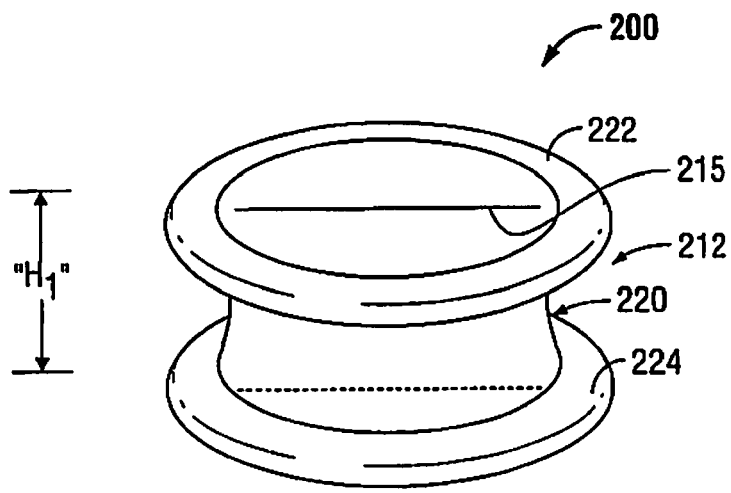
FIG. 5 is a perspective view of an access device according to an alternative embodiment of the present disclosure.
Figure 6:
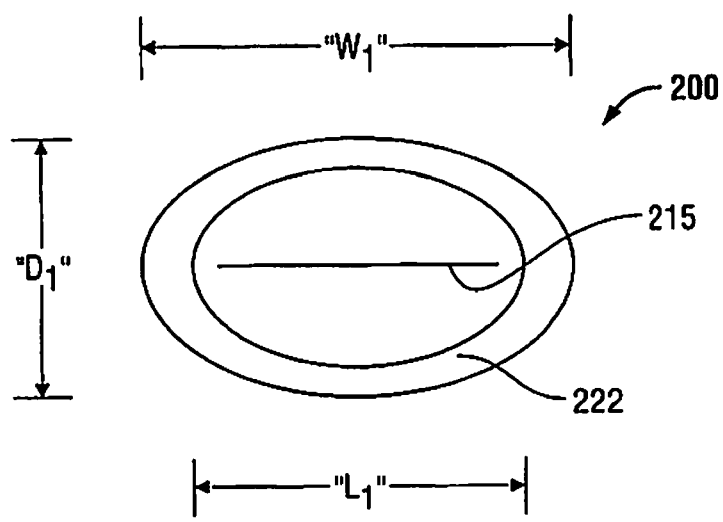
FIG. 6 is a top view of the access device of FIG. 5.

Turning now to FIGS. 5 and 6, an access device according an alternative embodiment of the present disclosure is shown generally as access device 200. Access device 200 is substantially similar to access device 100 described hereinabove, and will only be described as relates to the differences therebetween. Access device 100 includes a body 212 having a central portion 220, an upper rim 222 located on a proximal end thereof and a lower rim 224 located on a distal end thereof. Body 212 defines a slit 215 extending longitudinally through central portion 220. Each of upper and lower rims 222, 224 and central portion 220 define substantially oval members. The oval shape of upper and lower rims 222, 224 and central portion 220 permits a longer slit 215. In this manner, access device 200 is configured to more readily accommodate passage of hand "H". Upper and lower rims 222, 224 have a width "$W_1$" and a depth "$D_1$". Body 212 includes a height "$H_1$" and slit 215 includes a length "$L_1$". In one embodiment, upper and lower rims 222, 224 include a width "$W_1$" of about five inches (5") and a depth "$D_1$" of about three inches (3"), body 212 includes a height "$H_1$" of about three and one-half inches (3.5") and slit 215 includes a length "$L_1$" of about three inches (3").

It will be understood that various modifications may be made to the embodiments disclosed herein. For example, either or both of the upper and lower rims and the central portion may include selectively inflatable cavities configured to facilitate insertion and removal of the access device through an incision. Therefore, the above description should not be construed as limiting, but merely as exemplifications of particular embodiments. Those skilled in the art will envision other modifications within the scope and spirit of the claims appended hereto.

The invention claimed is:

1. An access device for insertion through an opening in tissue, the access device comprising:
   a body formed of a foam material, the body having:
      a central portion with a proximal end and a distal end;
      an upper rim located on the proximal end of the central portion; and
      a lower rim located on the distal end of the central portion,
      at least one of the upper rim or the lower rim having an oval cross-section relative to a longitudinal axis of the body when the body is in an at-rest state, the at least one of the upper rim or the lower rim defining a major axis and a minor axis, the body transitionable between a compressed condition adapted to facilitate insertion thereof through the opening in the tissue and an uncompressed condition adapted to secure the body within the opening in the tissue in a sealing relation, the at least one of the upper rim or the lower rim defining a slit between the upper and lower rims of the body, wherein the slit extends a substantial length of the at least one of the upper rim or the lower rim along the major axis, the slit extending between proximal and distal ends of the body.

2. The access device according to claim 1, wherein the central portion includes an oval cross-section.

3. The access device according to claim 1, wherein the body defines an hourglass shape.

4. The access device according to claim 1, wherein the upper and lower rims are integrally formed with the central portion.

5. The access device according to claim 2, wherein the central portion has the oval cross-section when the body is in the at-rest state.

6. The access device according to claim 1, wherein the oval cross-section of the at least one of the upper rim or the lower rim is transverse to the longitudinal axis of the body.

\* \* \* \* \*